United States Patent [19]

Gardiol et al.

[11] Patent Number: 5,654,164
[45] Date of Patent: Aug. 5, 1997

[54] METHOD AND DEVICE FOR REDUCING OXYGEN WITH A REDUCED OXIDASE WITH COLOR FORMATION

[75] Inventors: Alicia E. Gardiol, Montevideo, Uruguay; Ruben J. Hernandez; Bruce R. Harte, both of East Lansing, Mich.

[73] Assignee: Board of Trustees operating Michigan State University, East Lansing, Mich.

[21] Appl. No.: 662,537

[22] Filed: Jun. 13, 1996

Related U.S. Application Data

[63] Continuation of Ser. No. 370,403, Jan. 9, 1995.
[51] Int. Cl.$^6$ ..................................................... C12Q 1/26
[52] U.S. Cl. ........................... 435/25; 436/164; 436/904
[58] Field of Search .............................. 435/25, 183, 808, 435/810; 436/127, 164, 810, 904

[56] References Cited

U.S. PATENT DOCUMENTS

| | | | |
|---|---|---|---|
| 4,681,841 | 7/1987 | Matsumoto et al. | 435/18 |
| 5,180,672 | 1/1993 | Itoh et al. | 435/190 |

FOREIGN PATENT DOCUMENTS 3236766A  3/1991  Japan.

OTHER PUBLICATIONS

Andreasson, L., Kinetic Studies of Rhus vernicifera Laccase, Biochimica et Biophysica Acta 438 370–379. 1976.
Wollenberger, U., et al., Methods in Enzymol. vol. 137, Part D. Academic Press, Inc. (1986).
Varfolomeev, S.D., Methods In Enzymol. vol. 137, Part D. pp. 430–440, Academic Press, Inc. (1986).
Mattiasson, B., et al., Carbohydr. Res. 102:273 (1982).
Reinhammer, B. Laccase, pp. 2–31. In R. Lontie (ed). Copper Proteins and copper Enzymes. vol. III CRC (1984).
Reinhammer, B. Purif. and prop. of laccase and stell. from Rhus vernicifera. Biochim. Biophys. Acta. 205:35. (1970).
Oberbacher, M.F. and H.M. Vines. Spectrophotometric assay of ascorbic acid oxidase. Nature 197:1203–1204 (1963).
Leonowicz, A. and K. Grzywnowicz, Enzyme Microb. Technol. 3:55–58 (1981).
Peterson, L., and H. Degn. Steady–state kinetics of laccase from Rhus vernicifera. Biochim. Biophys. Acta. 526:85–92 (1978).
Perry, R.H. and C. H. Holton. Chemical Engineers Handbook. McGraw–Hill Book Co., New York. (1983). pp. 3–102.
Malmstrom, B.G., A. Finazzi Agro and E. Antonini European J. Biochem. 9:383–391 (1969).
Robertson, G.L. and C.M.L. Samaniego, J. Food Sci. 51:184–187 (1986).
Michaels, A.S. and H.J. Bixler, J. Polym. Sci. 50:413 (1961).
Andreasson, A., R. Branden, and B. Reinhammer, Biochim. Biophys. Acta. 438:370–379 (1976).
Messerschmidt, A., et al., Eur. J. Biochem. 187:341–352 (1990).
Guidelines for the characterization of immobilized biocatalysts. Enzyme Microb. Technol. 5:304–307 (1983).

*Primary Examiner*—Ralph Gitomer
*Attorney, Agent, or Firm*—Ian C. McLeod

[57] ABSTRACT

A method and device for removing oxygen using a reduced oxidase enzyme and for providing a colorimetrically detectable signal of the presence of the oxygen is disclosed. A reduced laccase or ascorbate oxidase is preferably provided with a substrate which reduces the oxidase. Color is generated which can be detected visually or by other means such as a spectrophotometer. The method and device are particularly useful in the food, pharmaceutical and biological industries.

25 Claims, 6 Drawing Sheets

METHOD AND DEVICE FOR REDUCING OXYGEN WITH A REDUCED OXIDASE WITH COLOR FORMATION

This is a continuation of application Ser. No. 08/370,403 filed on Jan. 9, 1995, currently pending.

BACKGROUND OF THE INVENTION

1. Field of the Invention

The present invention relates to a method and device for reducing oxygen present in a confined space with a reduced oxidase with color formation. In particular, the present invention relates to a method and device which detects oxygen in the confined space by means of a blue color resulting from oxidation by the oxygen of the reduced oxidase. The method and device is particularly useful in the food, pharmaceutical and biological industries.

2. Description of Related Art

Indicators can be used to monitor a wide variety of biological and chemical reactions and to control fluctuations in the concentration of oxygen inside a packaged product. One particular use is for fresh and minimally processed packaged foods which require control of the internal environment in particular oxygen concentration to insure their freshness and safety.

Enzymes, including the blue oxidases, laccase and ascorbate oxidase, have been used in oxidized form in biosensors fundamentally to detect substances in aqueous solution. Laccase has been incorporated in gelatin membranes to determine glucose and phenol (Wollenberger, U., et al., Methods in Enzymol. vol 137, Part D. Academic Press, Inc. (1986)) and electrodes which reduce oxygen have been obtained by adsorption of laccase on carbonic carriers (Varfolomeev, S. D., Methods in Enzymol. Vol. 137, Part D. pp. 430–440, Academic Press, Inc. (1986)). Ascorbate oxidase has been immobilized by affinity chromatography for assay of ascorbic acid (Mattiasson, B, et al., Carbohydr. Res. 102:273 (1982)).

Japanese Patent Appln. JP3236766A describes the use of ascorbate oxidase, a laccase phenol oxidase and an ascorbate substrate to deoxygenate a food containing the ascorbic acid. Oxygen is removed by the reduced oxidase to prevent the deterioration of the food. British Patent Appln. No. 2022249 describes a method where ascorbic acid is determined by means of the oxygen consumed from the reaction mixture and produced by an ascorbate oxidase. Neither method relates to provide a colorimetrically detectable response from the oxidase.

There is a need for a colorimetrically detectable response to the presence of oxygen while reducing the oxygen in a confined space, particularly at low concentrations (10% by volume or less). There is particularly a need for a method using a separate device which detects the presence of oxygen in a confined space where the presence of oxygen may be deleterious to a material in the confined space.

OBJECTS

It is therefore an object of the present invention to provide a method and device for removing oxygen from a confined space while providing a colorimetrically detectable indication or signal for the presence of the oxygen. Further, it is an object of the present invention to provide a method and device which is inexpensive to construct and use and which is reliable. These and other objects will become increasingly apparent by reference to the following description and the drawings.

BRIEF DESCRIPTION OF THE DRAWINGS

FIG. 5A shows the biosensor 10 response to an oxygen concentration of 1%. FIG. 5B shows the progress of the reaction of the substrate reduced enzyme (decolorized) with an oxygen concentration of 2%. The return of blue color of the oxidized enzyme was detected both, visually and spectrophotometrically at 610 nm. Assay conditions and absorbance readings at 610 nm were taken as described in Example 1.

DESCRIPTION OF PREFERRED EMBODIMENTS

Figure 1:
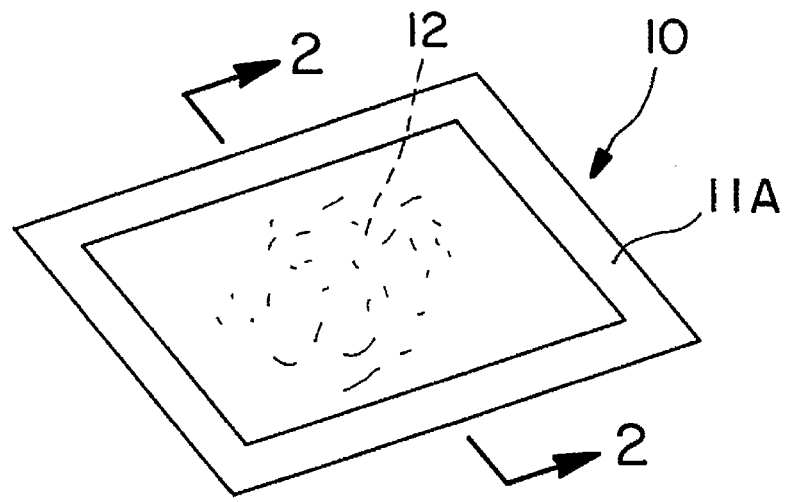
FIG. 1 is a perspective view of the sealed pouch 10 of the present invention including the reduced oxidase 12.

The present invention relates to a method which reduces oxygen gas in a confined space and provides a colorimetrically detectable indication of the presence of the oxygen gas which comprises: providing a reduced oxidase in an aqueous solution in the confined space; and exposing the reduced oxidase in the solution to oxygen gas, wherein the reduced oxidase is oxidized by the oxygen gas present in the solution to an oxidized oxidase thereby reducing the oxygen gas in the confined space and providing the colorimetrically detectable indication of the presence of the oxygen.

The present invention also relates to a device for the reaction of oxygen gas in a confined space and which provides a colorimetrically detectable indication of the presence of the oxygen gas which comprises: a confined space free of oxygen gas, wherein the confined space is provided with a means for introducing oxygen gas; and a reduced oxidase in an aqueous solution in the container in an amount which reacts with oxygen to provide the colorimetrically detectable indication of the presence of the oxygen.

Further, the present invention relates to a method for determining the presence of oxygen gas in a surrounding fluid to be tested for the oxygen gas which comprises: providing a reduced oxidase in an aqueous solution in a confined space; exposing the reduced oxidase in the solution to the oxygen gas in the surrounding fluid over time by introducing the oxygen into the confined space from the surrounding fluid, wherein the reduced oxidase is oxidized by the oxygen present in the surrounding fluid to an oxidized oxidase and the solution exhibits a change of light absorbance; and determining the change of light absorbance as a measure of the presence of the oxygen gas.

Finally the present invention relates to a test device for determining the presence of oxygen in a surrounding fluid and which provides a colorimetrically detectable indication of the presence of the oxygen which comprises: a container with an atmosphere free of oxygen gas wherein the container is provided with a means for introducing the oxygen gas into the container from the surrounding fluid; and a reduced oxidase in the aqueous solution in the container in an amount which reacts with oxygen to provide the colorimetrically detectable indication of the presence of the oxygen.

The method and devices are particularly useful in the food, biological and the pharmaceutical industries where oxygen can cause deterioration or spoilage. They are also useful for protecting chemicals which are oxygen sensitive. Other uses are to detect low oxygen concentration in any surface.

The temperature for reaction of the oxidase with oxygen is usually between 0° C. and 30° C. Preferably the temperature is between 2° C. and 25° C. Refrigeration temperatures are particularly preferred.

The reduced oxidase is preferably present at a concentration of between about 0.001 and 1 millimolar (mM). The substrate is present in an amount between about 4 and $10^6$ times the molar amount of the reduced oxidase. This insures that the oxidase is in fact reduced prior to contact with oxygen. Typically a metal chelating agent, such as EDTA, is used to prevent deterioration of the substrate, particularly ascorbate.

The blue oxidase enzymes are available from a variety of sources. In particular laccases are available from higher plants including *Rhus vernicifera; Rhus succedanea; Lactarius piperatus;* and *Prunus persica*. They are also available from fungi including *Polyporus versicolor* A, B; *Pleurotus; Pholiata; Podospora anserina; Neurospora crassa; Aspergillus nidulans;* White-rot fungi; and *Pyricularia oryzae*. The enzyme has its own chromophores. The prosthetic type 1 $Ca^{+2}$ which is responsible for the strong blue color, and the type 3 copper pair exhibiting a strong absorption based at 330 nm of the oxidized enzyme. The reduction and reoxidation reactions have second order kinetic constants of 250 $M^{-1}s^{-1}$ and $6\times10^6$ $M^{-1}s^{-1}$ respectively at pH 7.5 and 25° C. which indicates that the reactions take place at a very fast rate.

The reducing substrates are for instance: phenols, mono-, diphenols (catechol, resorcinol), and polyphenols, aminophenols, diamines, hexacyanoferrate (II), ascorbic acid and alkali metal ascorbates, particularly sodium ascorbate. Thus, various organic compounds which contain hydroxy, acidic or salt or amine groups can function as reducing substrates.

Ascorbate oxidase is a blue oxidase which is available from various plants including *Cucurbita pepo condensa* (yellow crook-neck squash); *Cucurbita pepo medullosa* (green zucchini squash); and *Cucumis sativus* (cucumber). It is also available from fungi including *Myrothecium verrucaria*.

The substrates for ascorbate oxidase are for instance: catechols, flavonoids, hydroxycinnamic acids, 2,6- and 2,5-dichlorohydroquinone, and 2,6-dichloroindophenol. Various organic compounds which contain acid, salt and hydroxy groups can be used.

The metal chelators are for instance: EDTA and porphyrins. Other metal binding compounds can be used so long as they do not interfere with the oxidase.

Figure 2:
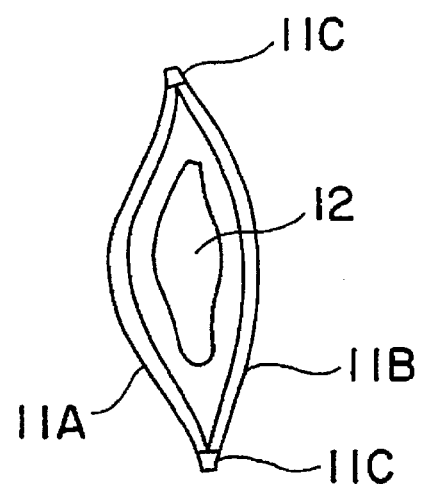
FIG. 2 is a cross-sectional view along line 2—2 of FIG. 1.

The device of the present invention is preferably enclosed in a container which is provided with an oxygen permeable film preferably in the form of a pouch. As shown in FIGS. 1 and 2, a device or pouch 10 is made of clear transparent plastic sheets 11A and 11B. The edges 11C are heat or otherwise sealed and contain the reduced oxidase substrate 12. The typical oxygen permeability values of selected polymer films at 25° C. Units: $cc.cm/cm^2s$ Pa are shown in Table 1.

TABLE 1

| POLYMER | PERMEABILITY × $10^{10}$ |
|---|---|
| Poly(ethylene), LDPE | 2,200 |
| HDPE | 300 |
| Poly(propylene) | 1,700 |
| Poly(styrene) | 1,900 |
| Polt(methyl methacrylate) | 120 |
| Poly(acrylonitrile) | 0.15 |
| Poly(acrylonitrile-co-styrene)86/14 | 3.2 |
| Poly(vinyl acetate) | 136 |
| Poly(ethylene-co vinyl alcohol) 30/70 | 0.3 |
| Saran ® | 3.8 |
| Poly(tetrafluoroethylene) | 3,200 |
| Poly(butadiene) | 14,300 |
| Poly(butadiene-co-acrylonitrile) | 6,150 |
| Natural rubber | 17,600 |
| Nylon 6 (dry) | 28 |
| Poly (ethylene terephathalate) | 26 |
| Cellophane | 1.6 |
| Ethyl cellulose | 11,000 |

A permeability of at least about 0.5 and between about 0.01 and 20,000 cubic centimeters of $O_2$×thickness surface area of the pouch×second×pressure in Pascal is needed for the pouch. The preferred range is 0.01 to 2,000.

In the following Examples 1 and 2, blue oxidase enzymes, including laccase and ascorbate oxidase, have a blue chromophore prosthetic group, type 1 $Cu^{+2}$, which can be reduced and decolorized with reducing substrates. When the enzyme is reoxidized with molecular oxygen there is a concomitant return of the enzyme blue color. The oxygen biosensor consisted of the *Rhus vernicifera* laccase enzyme reduced with substrate ascorbate under optimized assay conditions, under nitrogen and enclosed in pouches of low density polyethylene. Operational stability of the oxygen biosensor under a nitrogen atmosphere and refrigeration temperature was established. Gas-phase oxygen concentrations were measured following the rate of reappearance of the enzyme blue color, both visually and spectrophotometrically at 610 nm. The oxygen biosensor was able to detect a wide range of assayed oxygen concentrations. The time required to recover the enzyme blue color (biosensor response) with the optimized assay conditions, under refrigeration and at high water activity level was characterized. An oxygen biosensor is described with the adequate activity and Stability to measure gas-phase oxygen concentrations under refrigeration and at high water activity level. This oxygen biosensor is used to indicate increases, above acceptable levels in headspace oxygen concentration which could affect the quality and safety of products packaged under initial low levels of oxygen concentration.

*Rhus vernicifera* laccase, a multicopper blue oxidase as the oxygen detector, is preferred. Laccases from different sources, contain four copper ions, one type 1, one type 2, and two type 3. This enzyme couples the oxidation of substrate at the type 1 copper to the reduction of dioxygen to water at the type 2/type 3, trinuclear copper cluster site. The enzyme has its own chromophore, the prosthetic group type 1 $Cu^{+2}$ which is responsible for the strong blue color of the oxidized enzyme (Reinhammer, B. Laccase, pp. 2–31. In R. Lontie (ed). Copper Proteins and copper Enzymes. Vol. III. CRC Press. (1984)). The reduction of the enzyme by the substrate (decolorization) and reoxidation by oxygen (return of blue color) was followed visually and spectrophotometrically. Pouches of LDPE polymer support were used to enclose the enzyme/substrate system. The time of response of the ascorbate reduced enzyme (oxygen biosensor) to different gas-phase oxygen concentrations was characterized.

A gas-phase oxygen biosensor is described using a blue oxidase enzyme to detect specific increases in gas-phase oxygen concentration (e.g. 0 to 2%), under refrigeration temperature (5° C.) and at high water activity level with an adequate intensity and time of colorimetric response.

Purified *Rhus vernicifera* laccase (p-diphenol; $O_2$ oxidoreductase E.C. 1.10.3.2) was from B. Reinhammer (Reinhammer, B. Purification and properties of laccase and stellacyanin from *Rhus vernicifera*. Biochim. Biophys. Acta. 205:35. (1970)). Sodium ascorbate, syringaldazine and gelatin were obtained from Sigma Chemical Co. (St. Louis, Mo.). All other chemicals were of analytical grade quality.

EXAMPLE 1

PROTEIN DETERMINATION AND ACTIVITY ASSAY OF THE BLUE OXIDASE ENZYME

Protein content of the laccase enzyme preparation was determined spectrophotometrically at 611 nm, using a molar extinction coefficient of 5,700 $M^{-1}$ $cm^{-1}$ (Reinhammer, B. Laccase, pp. 2–31. In R. Lontie (ed.) Copper Proteins and Copper Enzymes. Vol III. CRC Press. (1984)).

Ascorbate oxidation activity of the laccase enzyme was determined by following the decrease in ascorbate absorbance at 265 nm (Oberbacher, M. F. and H. M. Vines. Spectrophotometric assay of ascorbic acid oxidase. Nature 197:1203–1204. (1963)) in a Perkin Elmer Lambda 4B spectrophotometer (Perkin Elmer, Oak Brook, Ill.). Buffer used was 0.1 M Potassium Phosphate, pH 5.8, 1 mM EDTA, saturated with air at room temperature. Controls containing only substrate were used to correct for substrate autooxidation.

Syringaldazine assays (Leonowicz, A. and K. Grzywnowicz. Quantitative estimation of laccase forms in some white-rot fungi using syringaldazine as a substrate. Enzyme Microb. Technol. 3:55–58. (1981)) were carried out in buffer 0.05 M Potassium Phosphate, pH 6.5, saturated with air at room temperature. The substrate syringaldazine was used at a final concentration of 6.4 µM. Activity showed an initial lag as previously described. Rates were expressed as the change in absorbance per minute at 525 nm corresponding to the formation of product. One unit of enzyme was defined as the amount of enzyme that produces a change of absorbance at 525 nm of 0.001 per minute under the standard assay conditions.

DEVELOPMENT AND CHARACTERIZATION OF THE GAS-PHASE OXYGEN BIOSENSOR

Substrate reduced enzyme under nitrogen

Oxidized (blue) laccase enzyme from *Rhus vernicifera* laccase was used. Enzyme and ascorbate solutions were initially equilibrated with a nitrogen atmosphere having an oxygen concentration lower than 20 ppm. The enzyme, 0.1 ml containing 1500 µg of protein, with an activity of 167 enzyme units was equilibrated with a current of nitrogen gas in a screw-capped glass vial under ice (0° C.). Ascorbate powder (15 mg) was first degassed under vacuum. Ascorbate solution was prepared (in the same screw-capped glass vial with rubber septum) by adding with a gas-tight syringe (Hamilton, Reno, Nevada), 1 ml of 0.1 M Potassium Phosphate buffer, pH 5.7, containing 3 mM EDTA, previously equilibrated with nitrogen gas. Enzyme was reduced with substrate by addition (with a gas-tight syringe) of the ascorbate solution (0.05 ml) to the enzyme solution (0.1 ml) in a screw-capped glass vial with a rubber septum.

Enclosement of the enzyme/substrate system

Low density polyethylene (LDPE) pouches 10 (0.7×3.0 cm) were made by heat sealing two sheets of LDPE (31.8× $10^{-6}$ m, thickness) (Dow Chemical, Midland, Mich.) with an impulse heat sealer (Marsh Instrument Co., Ill.) for 0.5 sec with a pressure of 340 kPa. To eliminate the oxygen gas sorbed by the film, LDPE pouches 10 were first equilibrated with nitrogen gas. Pouches 10 were then filled, using a gas-tight syringe, with the substrate reduced enzyme (0.15 ml) and sealed again.

Reaction with oxygen in gas-phase

Filled pouches 10 were immediately exposed to a gas atmosphere containing specific oxygen concentrations, in a sealed container, with a water saturated atmosphere, at 5° C. Containers were connected directly to a continuous flow of known oxygen concentration.

Gases of known oxygen concentration, nitrogen, 2% oxygen and 10% oxygen were used (Liquid Carbonic, Ill.). 1% oxygen concentration was prepared by dilution of the 2% oxygen concentration with nitrogen, using mass flowmeters (Sierra Instruments, Calif.) (Reinhammer, B. Purification and properties of laccase and stellacyanin from *Rhus vernicifera*. Biochim. Biophys. Acta. 205:35. (1970)). Oxygen concentrations in the reaction containers were checked with a gas-phase oxygen analyzer (Illinois Instruments, Ill.).

Characterization of the oxygen biosensor

The progress of the reaction with oxygen and the return of blue color of the oxidized enzyme was followed visually and spectrophotometrically at 610 nm. The rate of reappearance of the blue color (oxidized enzyme), during exposure of the decolorized (reduced) enzyme to a continuous flow of known oxygen concentration was determined spectrophotometrically at 610 nm. Pouches 10 of LDPE polymer containing the system were inserted in a special holder placed in the light path of a Perkin Elmer Lambda 3B spectrophotometer equipped with an integrating sphere attachment (Perkin Elmer, Oak Brook, Ill.). Absorbance values versus wavelength were recorded. Absorbance at 610 nm was calculated by subtracting the corresponding base line absorbance at 500 nm from the absorbance value at 610 nm for each sample.

The pouches 10 have adequate activity and stability properties as well as safety characteristics to be used in an oxygen biosensor. The system parameters were optimized to obtain maximum storage stability of the enzyme/substrate system and most adequate time and intensity of colorimetric response. A summary of the parameters selected or optimized for the oxygen biosensor is shown in Table 2.

TABLE 2

OPTIMIZED PARAMETERS

| | |
|---|---|
| ENZYME | *Rhus vernicifera laccase* |
| SUBSTRATE | Sodium ascorbate |
| POLYMERIC FILM | Low density polyethylene |
| POUCHES | 0.7 × 3.0 cm |
| ENZYME CONCENTRATION | 10 mg/ml = 0.09 mM |
| BLUE COPPER | 1 Type 1 $Cu^{+2}$/ enzyme = 0.09 mM |
| MOLAR EXTINCTION | 5,700 $M^{-1}$ $cm^{-1}$ at 611 nm |
| SUBSTRATE CONCENTRATION | 5 mg/ml = 25 mM |
| BUFFER | 0.1M Phosphate buffer, pH 5.7 |
| EDTA CONCENTRATION | 1 mM |
| TEMPERATURE | 5° C. |
| WATER ACTIVITY | Water saturation |

EXAMPLE 2

*Rhus vernicifera* laccase enzyme was selected (p-diphenol: $O_2$ oxidoreductase E.C. 1.10.3.2) as the blue oxidase because it has a strong blue color with an adequate molar extinction coefficient of 5,700 $M^{-1}$ $cm^{-1}$ at 611 nm (Reinhammar, B. Laccase, pp. 2–31. In R. Lontie (ed.) Copper Proteins and Copper Enzymes. Vol III. CRC Press. (1984)). An enzyme concentration of 10 mg/ml (0.09 mM), was chosen in order to obtain a visually detectable intensity of blue color when enclosed in LDPE pouches of dimensions (0.7×3.0 cm) in a final volume of 0.15 ml.

Storage stability of enzyme

Storage stability of the *Rhus vernicifera* laccase was investigated. The enzyme was kept at a concentration of 14 mg/ml (0.13 mM), in buffer 0.01 M Potassium Phosphate, pH 5.8, containing 1 mM EDTA.

The following conditions were tested:
(1) Enzyme in buffer solution at 5° C.
(2) Enzyme in buffer containing gelatin (5 mg/ml) at 5° C.
(3) Enzyme in buffer frozen at –20° C.

Figure 3:
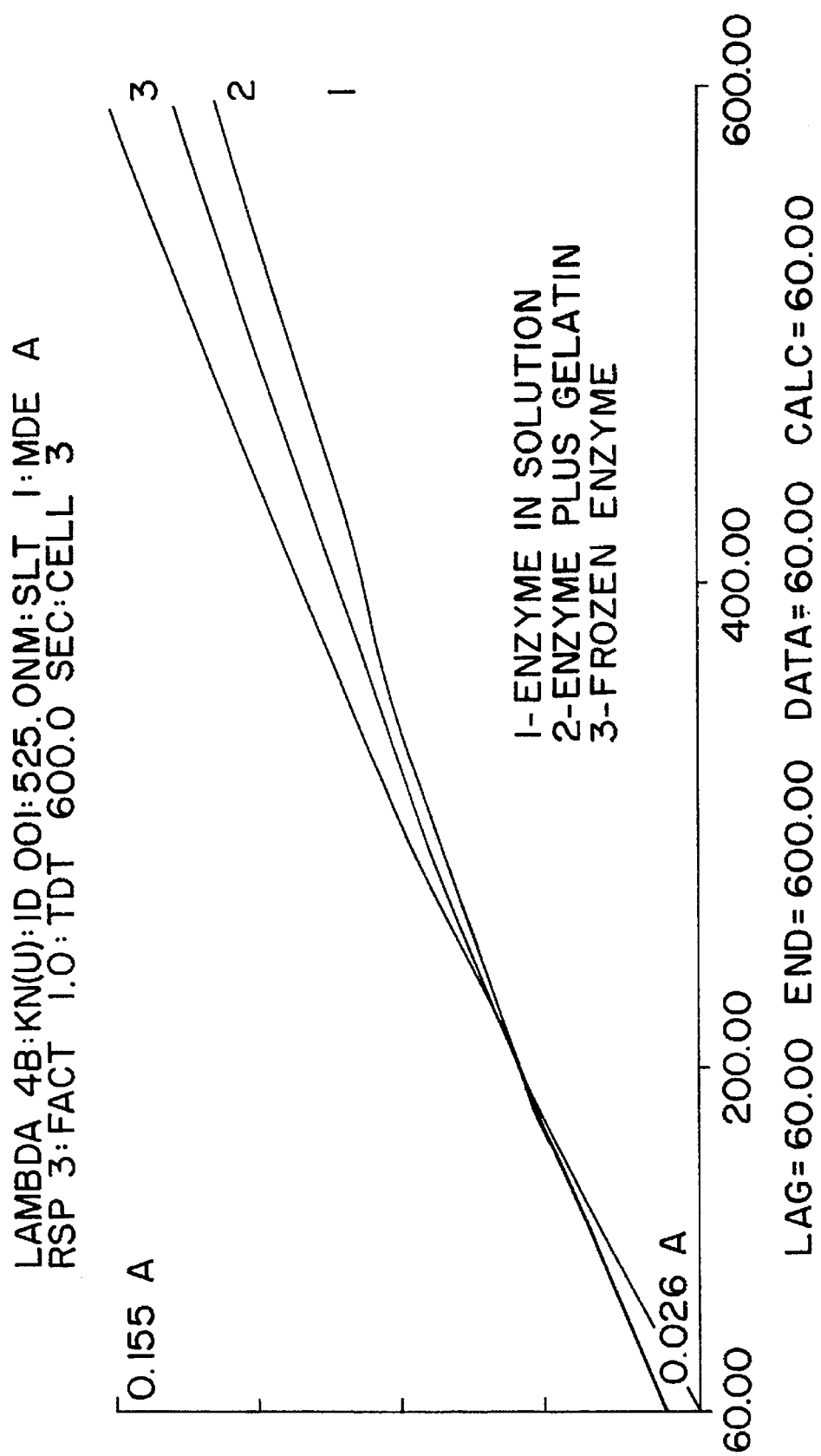
FIG. 3 is a graph showing storage stability of the blue oxidase enzyme using activity curves of the *Rhus vernicifera* laccase. The enzyme was maintained under the indicated conditions for 22 days. The reaction mixture is described in Example 1 and the amount of enzyme used was 140 µg.

Samples were taken at selected times and the enzyme activity was measured with the standard syringaldazine assay as described in Materials and Methods. Similar activity levels were maintained under the three conditions as indicated in Table 3 and FIG. 3.

TABLE 3

| ACTIVITY | 1 day | 3 days | 8 days | 15 days | 22 days |
|---|---|---|---|---|---|
| ENZYME SOLUTION | 0.028 (100%) | 0.028 (100%) | 0.015 (54%) | 0.014 (50%) | 0.012 (43%) |
| ENZYME + GELATIN | 0.025 (100%) | 0.024 (96%) | 0.015 (60%) | 0.014 (56%) | 0.012 (48%) |
| FROZEN ENZYME | 0.030 (100%) | | 0.023 (77%) | 0.016 (53%) | 0.016 (53%) |

ENZYME: *Rhus vernicifera* laccase
BUFFER: 0.01M Potassium phosphate pH 5.8, 1 mM EDTA.
CARRIER: Gelatin
TEMPERATURE: Refrigeration, 5° C.
OXYGEN CONCENTRATION: Atmospheric air, 20.9%
ASSAY: Standard syringaldazine assay
<sup>a</sup>*Rhus vernicifera* laccase was maintained under the three indicated conditions:
(1) in buffer solution, under refrigeration.
(2) in buffer plus gelatin, under refrigeration.
(3) in buffer, frozen at –20° C.
<sup>b</sup>Samples were taken at indicated times and enzyme activity was assayed with the standard syringaldazine assay as described in Materials and Methods of Example 1.
<sup>c</sup>Rates are expressed as the change in absorbance per minute at 525 nm.

The addition of gelatin did not increase stability and did not allow a good detection of the color change. Therefore, condition (1) buffer solution at 5° C. was selected to keep the enzyme in buffer solution at 5° C., as the standard operating conditions of the oxygen biosensor Enzyme which was kept frozen at –20° C. for 7 months had an activity level with the syringaldazine assay of approximately 50% of the initial activity. The enzyme activity of the frozen enzyme decreased to 53% of the initial value in 22 days, but it was maintained almost constant at 50% of the initial value after 7 months at –20° C. Therefore, freezing the enzyme in buffer at –20° C. provides a good storage method of the enzyme, which allows to obtain comparable results in experiments performed over a period of time of several months.

EXAMPLE 3

Enzyme activity with ascorbate as substrate

The laccase enzyme has a wide range of reducing substrates including sodium ascorbate, phenols, aminophenols and diamines (Reinhammer, B. Laccase, pp. 2–31. In R. Lontie (ed). Copper Proteins and Copper Enzymes. Vol III. CRC Press. (1984)). Although sodium ascorbate is not the best substrate for this enzyme in terms of reaction rate (Peterson, L., and H. Degn. Steady-state kinetics of laccase from *Rhus vernicifera*. Biochim. Biophys. Acta. 526:85–92. (1978)), it was selected because it is a natural and safe substrate from a food application standpoint.

The level of activity of the laccase enzyme with the substrate ascorbate was studied to establish the feasibility of the laccase/ascorbate system. With an ascorbate concentration of 0.2 mM and an enzyme concentration of 0.2 μM, an acceptable rate of ascorbate oxidation of 0.7 nmoles per minute per ml of reaction mixture was obtained. This corresponds to 0.35 nmoles of oxygen consumed per min per ml of reaction mixture. Activity values were corrected for substrate autooxidation. Oxygen concentration in the reaction mixture was the corresponding saturating level of atmospheric oxygen dissolved in the solution at room temperature ($1.27 \times 10^{-6}$ gmol/cc.atm) (Perry, R. H. and C. H. Hilton. Chemical Engineers Handbook. McGraw-Hill Book Co., New York. (1983)).

Autooxidation of ascorbate and levels of enzyme activity were both investigated with potassium phosphate buffer of the following pH values: 5.8, 6.5, 7.0, 7.5 and 8.0 containing EDTA. The presence of EDTA in the buffer significantly reduced autooxidation. Minimal autooxidation was obtained with the buffer containing EDTA of pH 5.8. There were no significant differences in the levels of enzyme activity within the range of pH from 5.8 to 8.0, and in the presence of EDTA. Therefore, the buffer 0.1 M Potassium Phosphate, pH 5.8 containing 1 mM EDTA, was selected to use in the oxygen biosensor.

EXAMPLE 4

To optimize the ascorbate concentration to be used in the oxygen biosensor, the following factors were considered.
(i) It has been reported that a complete decolorization of the laccase enzyme (which has one blue copper per enzyme molecule) by substrate under anaerobic conditions, is not achieved with less than 4 electron equivalents per molecule. In addition, the reoxidation by molecular oxygen gives a rapid return of blue color only when laccase is reduced by four electron equivalents (Malmstrom, B. G., A. Finazzi Agro, and E. Antonini. The mechanism of laccase-catalyzed oxidations; Kinetic evidence for the involvement of several electron-accepting sites in the enzyme. European J. Biochem. 9:383–391. (1969)).

Therefore, the ascorbate concentration in the biosensor should be in excess of 4 electron equivalents per blue $Cu^{+2}$. For an enzyme concentration of 0.1 mM, or 0.1 mM of blue $Cu^{+2}$, this corresponds to a concentration of electron equivalents of reducing substrate > than 0.4 mM.

(ii) Oxidative breakdown of ascorbic acid in liquids (in absence of enzyme) is complex, being dependent on pH, trace metals, light, initial dissolved oxygen concentration and temperature (Robertson, G. L. and C. M. L. Samaniego. Effect of Initial dissolved Oxygen Levels on the degradation of Ascorbic acid and the browning of lemon juice during storage. J.Food Sci. 51:184–187. (1986)). As indicated above the buffer pH and EDTA concentration to chelate metals for minimal ascorbate autooxidation were determined. The effect of light was eliminated by carrying out the reaction in the dark, in sealed containers under refrigeration. In the presence of both, oxygen and enzyme, and under refrigeration, the enzymatic oxidation reaction takes place at much faster rate than the autooxidation reaction.

(iii) The excess of ascorbate reducing equivalents with respect to type 1 blue $Cu^{+2}$ is enough to detect a wide range of oxygen concentration with different response times.

EXAMPLE 5

Low density polyethylene pouches 10 were used both, to contain the enzyme/substrate system in order to expose it to gas-phase oxygen and to provide a specific barrier to the transfer of oxygen into the enclosed system. The LDPE film has the adequate permeability barrier properties to prevent water loss from the pouches 10 and at the same time to control the diffusion of oxygen into the pouches 10. The water permeability of L74E is $1.9 \times 10^{-12}$ $cm^3$ (STP).cm/ $cm^2$.Pa.s at 5° C. (Michaels, A. S. and H. J. Bixler. J. Polym. Sci. 50:413. (1961)). The oxygen permeability of LDPE is $6.4 \times 10^{-14}$ $cm^3$ (STP).cm/$cm^2$.Pa.s at 5° C. and the oxygen diffusion coefficient is $1.4 \times 10^{-7}$ $cm^2$/s at 5° C. (Michaels, A. S. and H. J. Bixler. J.Polym. Sci. 50:413. (1961)). The solubility of oxygen in LDPE is $4.4 \times 10^{-6}$ $cm^3(STP)/cm^2$.Pa at 5° C. (Michaels, A. S. and H. J. Bixler. J. Polym. Sci. 50:413. (1961)). LDPE polymeric film also has the safety characteristics required for a food contact approved polymer by the Food and Drug Administration.

Oxidized (blue) enzyme was reduced with substrate ascorbate, under nitrogen and under the optimal conditions for system activity and stability (Table 2), and then exposed to varying oxygen concentrations in sealed LDPE pouches 10, under refrigeration (5° C.±1° C.) and at high water activity level.

The anaerobic reduction of laccase by different substrates, e.g. quinol, ferrocyanide, and ascorbate as well as the reoxidation of reduced laccase by molecular oxygen in aqueous solution with dissolved oxygen have been studied (Malmstrom, B. G., A. Finazzi Agro, and E. Antonini. The mechanism of laccase-catalyzed oxidations: Kinetic evidence for the involvement of several electron-accepting sites in the enzyme. European J. Biochem. 9:383–391. (1969); Petersen, L., and H. Degn. Steady-state kinetics of laccase from Rhus vernicifera. Biochim. Biophys. Acta. 526:85–92. (1978); Andreasson, A., R. Branden, and B. Reinhammar. Kinetic studies of Rhus vernicifera laccase. Biochim. Biophys. Acta. 438:370–379. (1976)) and provide a base of reference.

Figure 4:
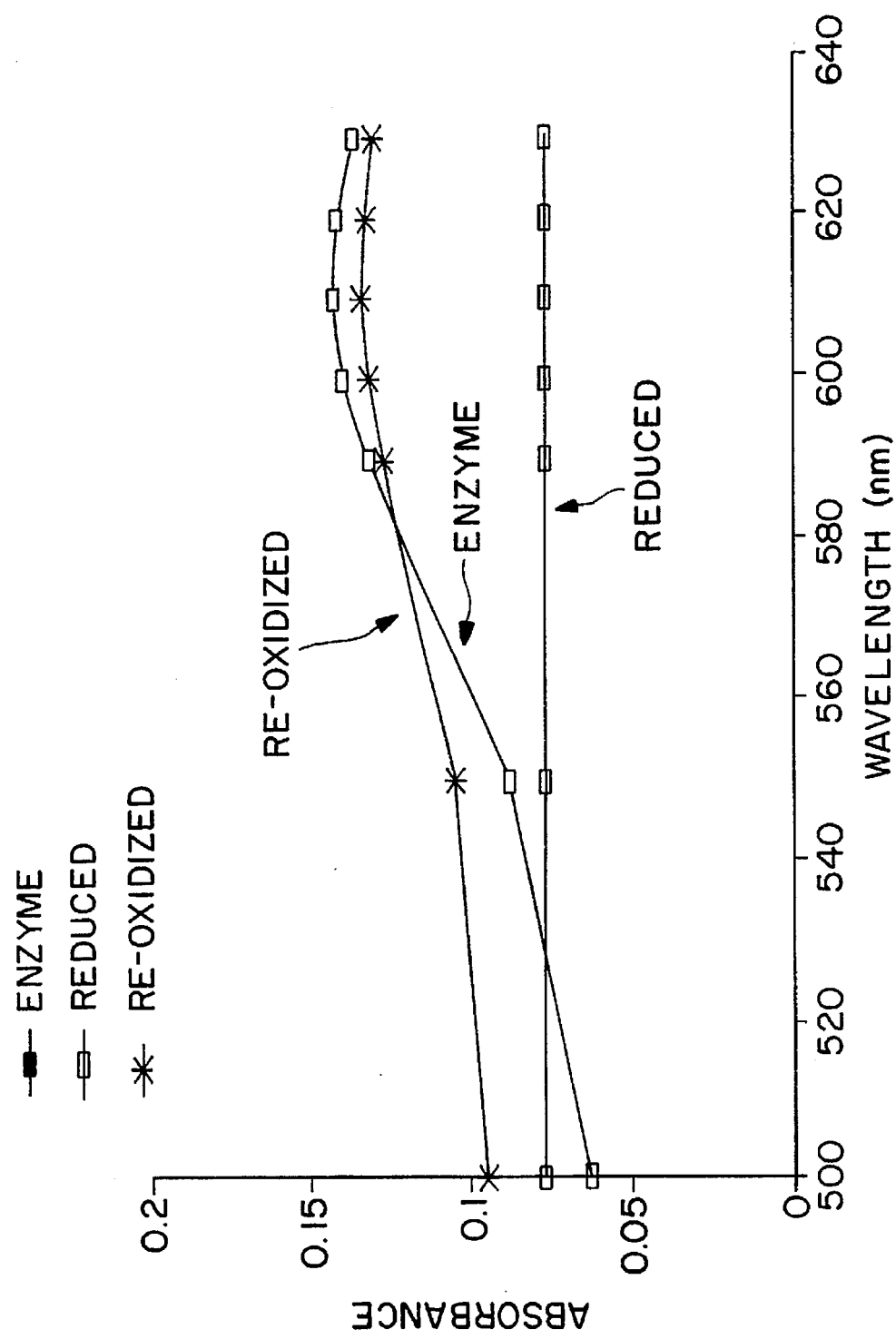
FIG. 4 is a graph showing reduction and reoxidation of the blue oxidase enzyme. Absorbance of the *Rhus vernicifera* laccase enzyme (filled squares) versus wavelength was followed spectrophotometrically. The blue chromophore (Type 1 $Cu^{+2}$) responsible for the enzyme blue color was reduced and decolorized (empty squares) with substrate ascorbate. As can be seen, the blue color was recovered by reoxidation (asterisks) with molecular oxygen.

The oxidized enzyme has a high absorbance at 610 nm due to the type 1 $Cu^{+2}$, responsible for the beautiful blue color of the blue oxidases. This absorbance peak disappears by reduction with substrate and returns by reoxidation with molecular oxygen. FIG. 4 shows the spectrum (Absorbance vs. wavelength) of the original oxidized Rhus vernicifera laccase enzyme (filled squares) enclosed in pouches 10 of LDPE, the substrate reduced enzyme (empty squares) and reoxidized enzyme (asterisks).

The enclosed enzyme/substrate assay system (oxygen biosensor) was able to detect a wide range of oxygen concentrations with a visually detectable change in color and a change of absorbance at 610 nm in the order of 0.030. Table 4 shows the corresponding time periods within which a positive response was obtained at each oxygen concentration.

TABLE 4

| OXYGEN CONCENTRATION | 24 h | 48 h | 72 h | 96 h | 120 h | 432 h |
|---|---|---|---|---|---|---|
| Nitrogen | − | − | − | − | − | − |
| 1% | − | − | − | − | + | + |
| 2% | − | − | + | + | + | + |
| 10% | + | + | + | + | + | + |
| Air | + | + | + | + | + | + |

A negative response was obtained with nitrogen during the time period studied. 10% oxygen and atmospheric air (20.9% oxygen) gave a positive response within 24 h.
<sup>a</sup>The substrate reduced enzyme enclosed in LDPE pouches 10 was exposed to a continuous flow of known oxygen concentrations in a sealed container under refrigeration.
<sup>b</sup>Indicated times correspond to the time periods within which a positive response of the biosensor or recovery of the enzyme blue color was obtained.

Figure 5A:
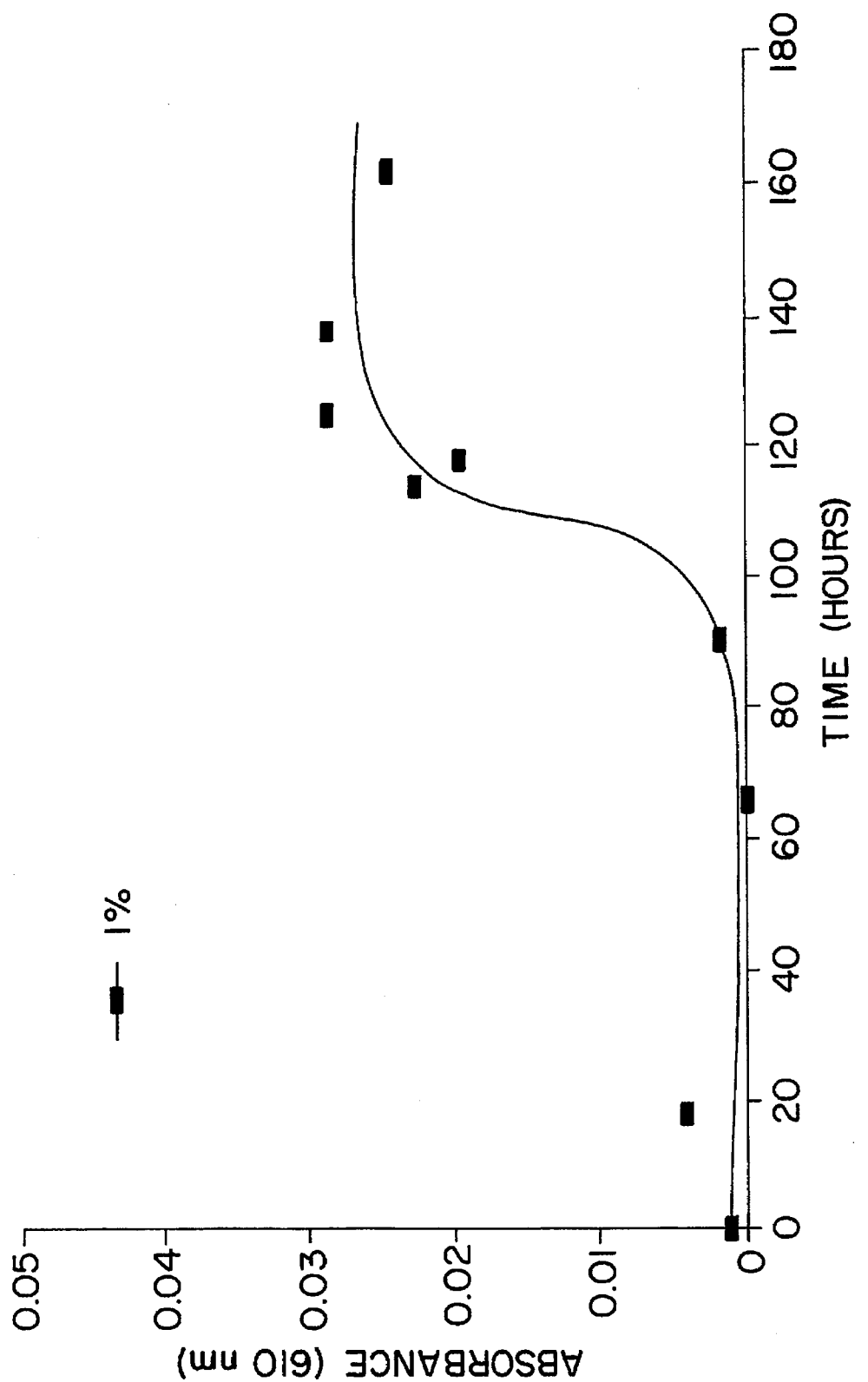
FIGS. 5A and 5B are graphs showing the biosensor 10 response to oxygen at different concentrations.
Figure 5B:
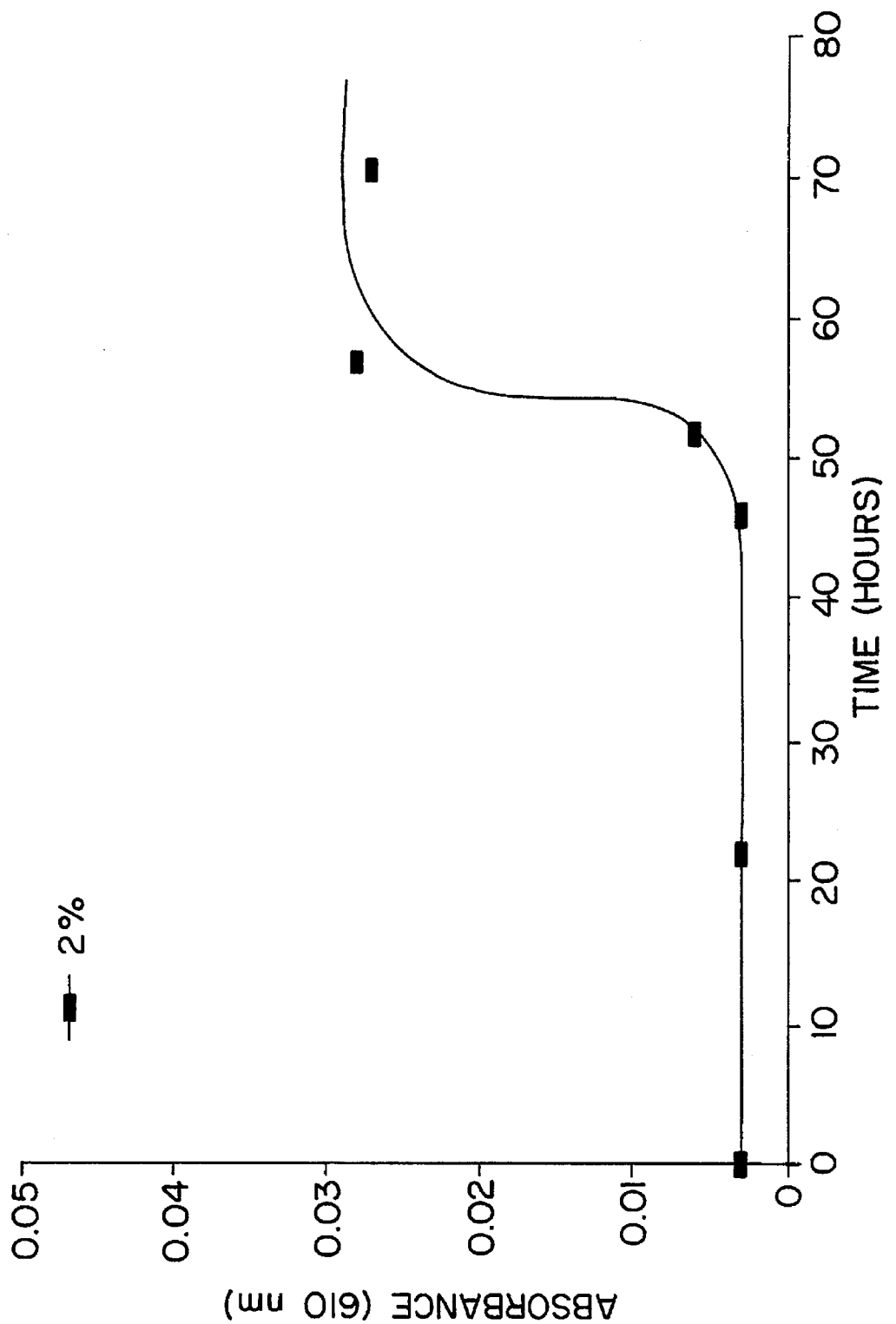

FIGS. 5A and 5B show the response of the biosensor to oxygen concentrations of 1 and 2% respectively. The blue color, with a change of absorbance of 0.026±0.002 (mean value±standard deviation) was recovered in 57 h for an oxygen concentration of 1% and a change of absorbance of 0.029±0.0007 (mean value±standard deviation) was obtained in 127 h for an oxygen concentration of 2% respectively. Standard deviation of the response time was ≦ than 6% of the mean value.

The laccase enzyme did not show a saturation kinetics with low substrates such as ascorbate and hydroquinone in solution (Peterson, L., and H. Degn. Steady-state kinetics of laccase from Rhus vernicifera. Biochim. Biophys. Acta. 526:85–92. (1978)). For each specific ratio of enzyme/substrate concentration the time of return of enzyme blue color as a function of oxygen concentration must be determined empirically.

EXAMPLE 6

The same batch of enzyme (kept frozen at −20° C. for 7 months) was used for experiments with oxygen concentrations of 1 and 2%. Enzyme used for the stability assay which was kept frozen under the same conditions, retained an activity of 50% of the initial value. After finishing these experiments, samples were collected and dialyzed against 0.01 M Potassium Phosphate buffer pH 5.8 for 48 h. This batch of dialyzed enzyme still gave a positive response to 10% oxygen concentration within 24 h. This confirms that the enzyme has the adequate stability to be used in the oxygen biosensor.

EXAMPLE 7

Ascorbate oxidase (L-ascorbate: $O_2$ oxidoreductase E.C. 1.10.3.3.) from Cucurbita species (Boehringer Mannheim Biochemicals, Indianapolis, Ind.) was also able to substitute for laccase in the oxygen biosensor. This enzyme has 2 Type 1 $Cu^{+2}$ per enzyme molecule (Messerschmidt, A., et al (Eur. J. Biochem. 187:341–352 (1990)). Enzyme (0.037 mM) was reduced with excess of ascorbate substrate (25 mM) and enclosed in LDPE pouches under the same conditions indicated in Table 2 for the laccase enzyme. The recovery of the blue color when exposed to 2% oxygen, was visually detectable at 53 h. This time response is very similar to the one obtained with the *Rhus vernicifera* laccase (FIG. 5B). Ascorbate oxidation with this enzyme is many orders of magnitude faster than with laccase. Therefore, this result supports the premise that the response time is mainly determined by the time required to permeate the necessary amount of oxygen through the polymeric film.

Figure 6:
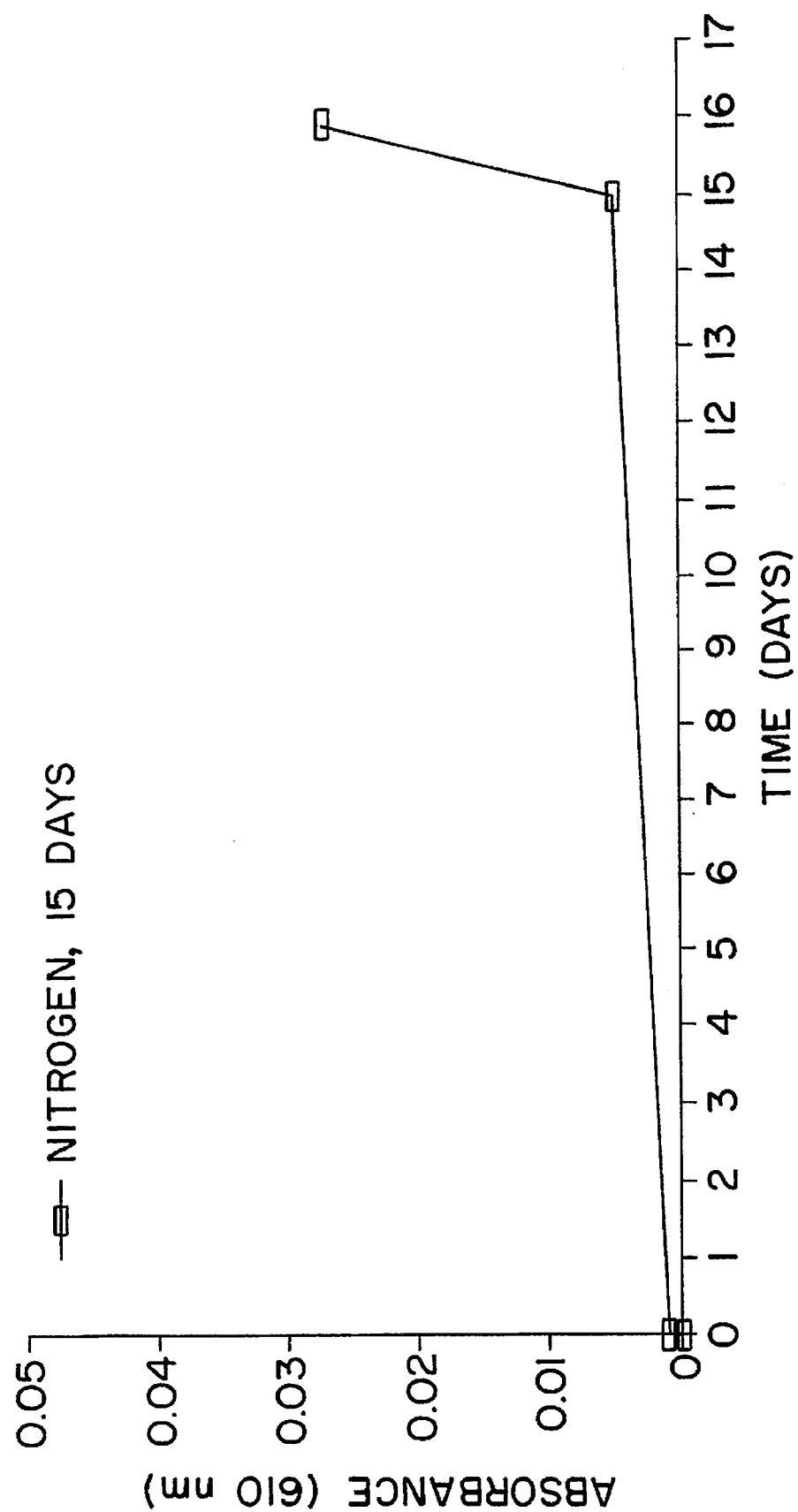
FIG. 6 is a graph showing operational stability of the system in the pouches. The enzyme/substrate system enclosed in LDPE pouches under refrigeration was maintained under nitrogen for 15 days and then exposed (arrow) to 10% oxygen concentration with a positive response within 24 hours.

Operational stability of the system (Guidelines for the characterization of immobilized biocatalysts. Enzyme Microb. Technol. 5:304–307. (1983)) was established. The substrate reduced enzyme was enclosed in LDPE pouches and kept for 15 days under operational conditions, under nitrogen, at 5° C., without any detectable change in color. A positive response was obtained within 24 h when the system was exposed to an oxygen concentration of 10%. The corresponding results are shown in FIG. 6. Therefore, under refrigeration temperature, and in absence of oxygen, the system had good operational stability, remained stable (with no detectable change in color) and active (able to respond to oxygen in gas phase).

The blue color of the oxidized enzyme was also stable under operational conditions and the final absorbance readings obtained for the 1 and 2% oxygen concentrations (read for 4 days) at 610 nm were constant.

The ascorbate substrate concentration allows differentiation of a wide range of oxygen concentrations with clearly different reaction times. Lower amount of substrate should be used to detect low oxygen concentrations in a shorter time.

The selection of polymeric films with different oxygen permeability coefficients would also allow to control the rate of the reaction and therefore the return of the blue color.

The data was based on an initial ascorbate concentration of 25 mM. The concentration of enzyme was 0.1 mM which corresponded to 0.1 mM equivalents of type 1 $Cu^{+2}$. Based on the consideration that 4 equivalents of reducing substrate are needed per type 1 $Cu^{+2}$, 0.4 mM equivalents of ascorbate are needed to decolorize 0.1 mM copper equivalents. Therefore, 24.6 mM equivalents of ascorbate have to be oxidized to recover the blue color. This requires 12.3 μmoles/ml of oxygen or 1.85 μmoles/0.15 ml. Oxygen permeability through LDPE is $6.4 \times 10^{-14}$ $cm^3.cm/cm^2.s.Pa$. From this value the time required to permeate the required amount of oxygen can be calculated.

$t = Q.l/P.A.\Delta p$
$Q = 1.85 \times 10^{-6}$ moles
$l = 31.8 \times 10^{-6}$ m
$P = 6.4 \times 10^{-14}$ $cm^3.cm/cm^2.s.Pa$
$A = 0.7 \times 3.0 \times 2$ $cm^2$
Delta p=atm This value is dependent on the oxygen concentration and is limiting the rate of response of the oxygen biosensor.

Thus the present invention particularly relates to an oxygen biosensor with the adequate activity and stability to measure oxygen concentration, when exposed to oxygen in gas phase, for a selected range of oxygen concentration, under refrigeration, and at high water activity level.

It is intended that the foregoing description be only illustrative of the present invention and that the present invention be limited only by the hereinafter appended claims.

We claim:

1. A method which reduces oxygen gas in a confined space and provides a colorimetrically detectable indication of the presence of the oxygen gas in the confined space which comprises:
   (a) providing a reduced oxidase in an aqueous solution in the confined space, wherein the reduced oxidase is reactive with oxygen gas introduced into the confined space;
   (b) exposing the reduced oxidase in the aqueous solution to oxygen gas introduced into the confined space, wherein the reduced oxidase is oxidized by the oxygen gas to an oxidized oxidase thereby reducing the oxygen gas in the confined space and providing the colorimetrically detectable indication of the presence of the oxygen;
   (c) determining the light absorbance of the oxidized oxidase; and
   (d) correlating the light absorbance of the oxidized enzyme to the pressure of oxygen in the confined space.

2. The method of claim 1 wherein the oxidase is a laccase.

3. The method of claim 1 wherein the oxidase is a laccase from *Rhus vernicifera* and the oxidized oxidase in the aqueous solution is blue in color when exposed to light at 610 nm.

4. The method of any one of claims 1 to 3 wherein the exposing in step (b) is at a temperature between about 0° to 30° C.

5. The method of claim 1 wherein in step (a) reduced oxidase is prepared by reducing the oxidase with a substrate for the oxidase in an aqueous solution.

6. The method of claim 5 wherein the substrate is an ascorbate salt.

7. The method of claim 6 wherein the ascorbate salt is sodium ascorbate.

8. The method of claim 5 wherein a chelating agent is provided in the solution.

9. The method of claim 8 wherein the chelating agent is ethylenediamine tetraacetic acid.

10. A method for determining the presence of oxygen gas in a surrounding fluid containing a material which is deleteriously affected by the oxygen gas which comprises:
   (a) providing a reduced oxidase in an aqueous solution in a confined space separated from the surrounding fluid, wherein the confined space is provided with a means which allows permeation of the oxygen gas from the surrounding fluid;
   (b) exposing the reduced oxidase in the solution to the oxygen gas from the surrounding fluid by permeation through the means into the confined space from the surrounding fluid, wherein the reduced oxidase is oxidized by the oxygen present in the surrounding fluid to an oxidized oxidase and the solution exhibits a change of light absorbance due to the oxidized oxidase in the aqueous solution;
   (c) determining a change of the light absorbance of the oxidized oxidase, which is directly measured as a measure of the presence of a predetermined concentration of the oxygen gas which permeates into the confined space from the surrounding fluid
   (d) determining the light absorbance of the oxidized oxidase; and
   (e) correlating the light absorbance of the oxidized oxidase to the presence of oxygen in the surrounding fluid.

11. The method of claim 10 wherein the oxidase is a laccase.

12. The method of claim 10 wherein the oxidase is a laccase from *Rhus vernicifera* and the oxidized oxidase in the aqueous solution is blue in color when exposed to light at 610 nm.

13. The method of any one of claims 10, 11 or 12 wherein the exposing in step (b) is at a temperature between about 0° to 30° C.

14. The method of any one of claims 10, 11 or 12 wherein in step (a) the oxygen with the reduced oxidase is provided in a closed container as the confined space which allows visualization of the oxidized oxidase.

15. The method of any one of claims 10, 11 or 12 wherein the confined space is a plastic pouch which allows the oxidized oxidase to be viewed visibly and the oxygen gas to diffuse into the solution from the surrounding fluid.

16. The method of any one of claims 10, 11 or 12 wherein the reduced oxidase is present in a concentration between about 0.001 and 1 μm and wherein a substrate for the reduced oxidase is present in an amount between about 4 and $10^6$ times the molar amount of the reduced oxidase.

17. The method of any one of claims 10, 11 or 12 wherein the reduced oxidase is reduced laccase and is present in a concentration between about 0.001 and 1 μm and wherein a substrate for the reduced laccase is present in an amount between about 4 and $10^6$ times the molar amount of the reduced laccase and wherein the substrate is an ascorbate salt.

18. The method of claim 10 wherein in step (a) reduced oxidase is prepared by reducing the oxidase with a substrate for the oxidase in an aqueous solution.

19. The method of claim 18 wherein the substrate is an ascorbate salt.

20. The method of claim 19 wherein the ascorbate salt is sodium ascorbate.

21. The method of claim 18 wherein a chelating agent is provided in the solution.

22. The method of claim 21 wherein the chelating agent is ethylenediamine tetraacetic acid.

23. The method of claim 18 wherein steps (a) and (b) are at a temperature between about 2° and 25° C.

24. The method of claim 10 wherein the color is determined spectrophotometrically.

25. The method of claim 24 wherein in step (a) the oxygen with the reduced oxidase is provided in a closed container as the confined space, which allows a visualization of the color of the solution due to the oxidized oxidase.

* * * * *

UNITED STATES PATENT AND TRADEMARK OFFICE
CERTIFICATE OF CORRECTION

PATENT NO. : 5,654,164
DATED : August 5, 1997
INVENTOR(S) : Alicia E. Gardiol, Ruben J. Hernandez, and Bruce R. Harte It is certified that error appears in the above-identified patent and that said Letters Patent is hereby corrected as shown below:

Column 12, line 20 (Claim 1), "pressure of oxygen" should read --presence of oxygen--.

Signed and Sealed this

Fifth Day of May, 1998

*Attest:*

BRUCE LEHMAN

*Attesting Officer*     Commissioner of Patents and Trademarks